United States Patent
Romain et al.

(10) Patent No.: US 12,153,126 B2
(45) Date of Patent: Nov. 26, 2024

(54) DEVICE FOR CHARACTERIZING THE ACTIMETRY OF A SUBJECT IN REAL TIME

(71) Applicants: ECOLE NATIONALE SUPERIEURE DE L'ELECTRONIQUE ET DE SES APPLICATIONS, Cergy (FR); CENTRE NATIONAL DE LA RECHERCHE SCIENTIFIQUE, Paris (FR); THE UNIVERSITY COURT OF THE UNIVERSITY OF GLASGOW, Glasgow (GB); CY CERGY PARIS UNIVERSITÉ, Cergy (FR)

(72) Inventors: Olivier Romain, Montgeron (FR); Julien Lekernec, Quimperle (FR); Jordane Lorandel, Conflans Sainte Honorine (FR); Francesco Fioranelli, Delft (NL)

(73) Assignees: ECOLE NATIONALE SUPERIEURE DE L'ELECTRONIQUE ET DE SES APPLICATIONS, Cergy (FR); CENTRE NATIONAL DE LA RECHERCHE SCIENTIFIQUE, Paris (FR); THE UNIVERSITY COURT OF THE UNIVERSITY OF GLASGOW, Glasgow (GB); CY ENERGY PARIS UNIVERSITE, Cergy (FR)

( * ) Notice: Subject to any disclaimer, the term of this patent is extended or adjusted under 35 U.S.C. 154(b) by 413 days.

(21) Appl. No.: 17/766,760

(22) PCT Filed: Oct. 7, 2020

(86) PCT No.: PCT/EP2020/078161
§ 371 (c)(1),
(2) Date: Apr. 6, 2022

(87) PCT Pub. No.: WO2021/069518
PCT Pub. Date: Apr. 15, 2021

(65) Prior Publication Data
US 2023/0184924 A1    Jun. 15, 2023

(30) Foreign Application Priority Data

Oct. 7, 2019 (EP) .................................. 19306308

(51) Int. Cl.
*G01S 13/89* (2006.01)
*G06V 10/764* (2022.01)
*G08B 21/04* (2006.01)

(52) U.S. Cl.
CPC ............ *G01S 13/89* (2013.01); *G06V 10/764* (2022.01); *G08B 21/0446* (2013.01)

(58) Field of Classification Search
CPC .......... G01S 13/89; G01S 7/417; G01S 13/88; G06V 10/764; G08B 21/0446; A61B 5/1117; A61B 5/7264
See application file for complete search history.

(56) References Cited

U.S. PATENT DOCUMENTS

2020/0090322 A1*  3/2020  Seo ........................ G06N 3/084

FOREIGN PATENT DOCUMENTS

CN         105259553 A  *  1/2016

OTHER PUBLICATIONS

Translation of International Search Report & Written Opinion in PCT/EP2020/078161 dated Dec. 14, 2020, 8 pages.

(Continued)

*Primary Examiner* — Timothy A Brainard
*Assistant Examiner* — Ismaaeel A. Siddiquee
(74) *Attorney, Agent, or Firm* — Tucker Ellis LLP (57) ABSTRACT

The invention discloses a device (1) for characterizing in real time the actimetry of a subject, having: a radar (2) emitting and receiving radar signals, and having a software interface for configuring the shape of the signal emitted; processing and computing means (3) coupled to the radar (2), having a trained classifier (3a) using a database, said processing and computing means (3) being configured to perform in real time: —a capture of color micro-Doppler images (6) having several color channels (R, V, B), each having micro-Doppler signatures (6a) with color pixels the (Continued)

value of which is a function of a reflectivity and a speed of the subject; —a processing of the micro-Doppler images (6) for: computing a so-called monochromatic image having monochromatic pixels, each having a given monochromatic intensity, on the basis of the color pixels of each color micro-Doppler image; transforming the monochromatic image into a binary image by segmentation, according to a binary luminous intensity threshold, of the monochromatic pixels, producing binary pixels, the value of which is dependent on the chromatic intensity of the monochromatic pixel associated with the binary pixel, with respect to the threshold.

20 Claims, 5 Drawing Sheets (56) References Cited

OTHER PUBLICATIONS

Amin, et al. "Radar Signal Processing for Elderly Fall Detection." IEEE Signal Processing Magazine., vol. 33, No. 2, pp. 71-80, Mar. 2016.

Cippitelli, et al. "Radar and RGB-depth sensors for fall detection: A Review." IEEE Sensors Journal. vol. 17, No. 12. Apr. 20, 2017. pp. 3585-3604.

He, et al. "Human Fall Detection Based on Machine Learning Using a THz Radar System." 2019 IEEE Radar Conference. Apr. 22, 2019. pp. 1-5.

Wu, et al. "Radar-based Fall Detection Based on Doppler time-frequency signatures for assisted li." IET Radar Sonar Navigation, The Institution of Engineering and Technology, UK, vol. 9, No. 2. Feb. 1, 2015. pp. 164-172.

Javier, et al. "Application of Linear Predictive Coding for Human Activity Classification Based on Micro-Doppler Signatures." IEEE Geoscience and Remote Sensing Letters, IEEE Service Center, New York, NY. vol. 11, No. 10. Oct. 1, 2014. pp. 1831-1834.

Fioranelli, et al. "Bistatic human micro-Doppler signatures for classification of indoor activities." 2017 IEEE Radar Conference. May 8, 2017. pp. 610-615.

Debes, et al. "Monitoring Activities of Daily Living in Smart Homes: Understanding human behavior." IEEE Signal Processing Magazine., vol. 33, No. 2, pp. 81-94, Mar. 2016. pp. 81-94.

Freund, et al. "Large Margin Classification Using the Perceptron Algorithm." Machine Learning. vol. 37. 1999. pp. 277-296.

Jokanovic, et al. "Fall Detection Using Deep Learning in Range-Doppler Radars." IEEE Transactions on Aerospace and Electronic Systems., vol. PP, No. 99, Aug. 2017. 12 pages.

Otsu, Nobuyuki. "A Threshold Selection Method from Gray-Level Histograms." IEEE Transactions on Systems, Man, and Cybernetics. vol. SMC-9, No. 1. , pp. 62-66 Jan. 1979.

U.S. Department of Health and Human Services. "Report to Congress: Aging Services Technology Study." Jun. 2012. 202 pages.

* cited by examiner

- Class 1: fall
- Class 2: search for an object under a chair
- Class 3: Parkinson
- Class 4: pick up an object
- Class 5: sitting on ground
- Class 6: sitting on a chair
- Class 7: tying of shoelaces
- Class 8: TUG
- Class 9: walking
- Class 10: walking with carried object

DEVICE FOR CHARACTERIZING THE ACTIMETRY OF A SUBJECT IN REAL TIME

FIELD OF THE INVENTION

This invention relates to a device for characterizing the actimetry of a subject in real time.

PRIOR ART

In the past few years automatic posture detection has given rise to intense research activity and major economic repercussions. "Kinect"-type 3D sensors in particular have caused a paradigm shift in the gaming industry by offering the possibility of including depth information (3D) and thus more effectively discriminating the different types of movements of the subjects.

Today most of these systems of motion measurement and analysis are found in both the world of virtual animation (walking simulation) and in the biomechanical and medical field.

These systems make it possible to study problems of detection of pathology in the subject, to analyze the body in activity, or to understand walking mechanisms.

However, the academic competitions based on this theme organized very recently show the limitations of current sensors, particularly for the recognition of postures in various situations and in particular falls of deficient subjects.

Current systems can be grouped into three categories; onboard systems on a subject, remote systems and hybrid systems (mixture of onboard and remote).

Many onboard technologies have been proposed for the monitoring of subjects and specifically for fall detection [3] over the past thirty years. These include wearable devices such as podometers, locometers, accelerometers, gyroscopes and panic buttons, inertial sensors such as smartphones, and sensors which are infrared, vibrating, acoustic, magnetic etc.

Although these devices give good results [4] on fall identification (98%), most of these solutions onboard the subject suffer from several major problems [2] which limit their uses:

They must be worn, which depends on the compliance of the user or the user remembering to put it on if they wake up at night to go to the toilet.
They are easily breakable in the event of a fall, an impact or being sat on.
They must be recharged, which can be difficult for subjects with a cognitive impairment.
The rate of false alarms.
They are stigmatizing for subjects.
They are not respectful of privacy (according to some).

Remote devices are generally based on the use of measurement systems incorporated into the living environment of the user. This includes video cameras [5], moving walkways, RGB-D (Red, Green, Blue Detector, according anglosaxon terminology) photographic sensors and radars or a combination of these systems. Whole apartments can be equipped with PIR (Passive InfraRed) sensors), gas stove sensors, sensors in the bed, sensors on the floor etc., which can be used to give outlines of everyday living activities. However, they are not capable of giving more fine-grained information on gait analysis for the detection of changes.

Figure 1:
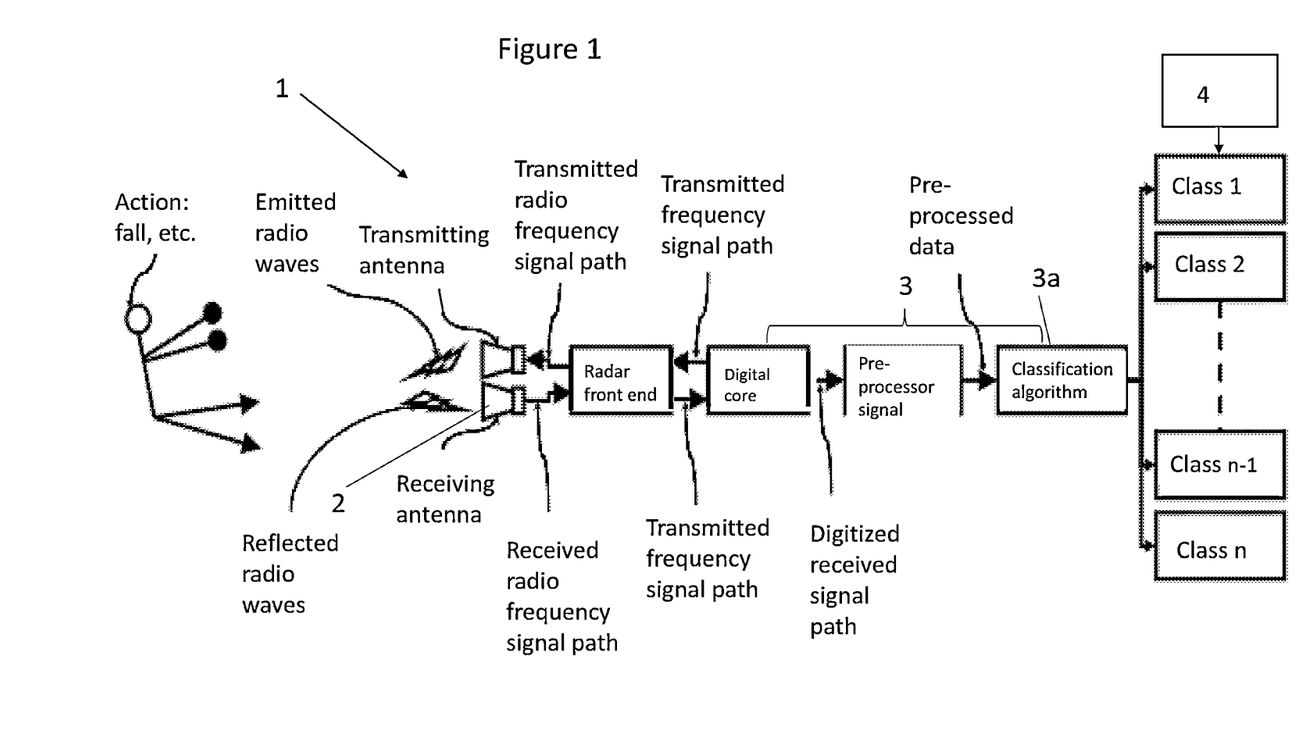
FIG. 1 shows a principle diagram of the invention.

For radar and RGBI-D systems, there are clear challenges to be met regarding the deployment and use of these systems in practical scenarios in the home or in specialist institutions:

Regarding video cameras [6], the main challenges to be met are still occlusions (areas of dead pixels), night functionality, 3D areas of dead pixels, accuracy, camera resolution, and respect of privacy. The monitoring of subjects in their daily life poses a real problem of confidentiality (FIG. 1). Specifically, the perception of intrusion and the respect of privacy differ according to the sensor. This perception is expressed as a modification of the behavior and the addition of Concerning radar systems [7], the indoor environment liable to generate multi-path targets and the regulation of emissions are restrictive.

Although there are more technological challenges with radar, the fact that there is no legal problem concerning image copyright and no image is taken of the subject, thus respecting privacy, facilitates acceptance by end users and investors. For the abovementioned reasons, the radar arrangement is a beneficial avenue of research still unused in specialist environments (residential care home for the elderly), in penitentiary environments or in smart homes.

Radar is considered as an emerging technology for health monitoring and fall detection in assisted living due to a certain number of attributes not shared by other detection arrangements. The most common method for classifying activities is based on the extraction of characteristics resulting from micro-Doppler signatures (spectrogram). The relative motion of the structural components of an object/body generates unique pixel areas in the time-frequency domain of radar return signals. Consequently, different activities generate unique distinctive characteristics in micro-Doppler signatures which can be used for classification. In general, individuals measure and extract different characteristics of the spectrograms (slow time, Doppler), followed by various automatic classifications. The techniques for automatic classification comprise Fisher Discriminant Analysis (FDA), K Nearest Neighbors (KNN), Naive Bayes (NB) classification, and Support Vector Machines (SVM).

Recently, with the increase in computing power, it has become possible to use "deep learning" methods. "Deep learning" consists of all automatic learning methods, supervised or unsupervised, and is capable of automatically determining the most relevant characteristics for classification purposes.

For example, to recognize a face in vision by a computer with Convolutional Neural Networks (CNN), the first layer can recognize edges with different angles, then in the second layer different parts of the face (eyes, mouth, nose), then superimpose whole faces and then try to classify what it sees.

Another class of deep learning architecture used for natural speech processing are recurrent neural networks (RNN) with gated recurrent units and long short-term memory (LST).

Most of these approaches can be used to prove that the processing of signals from spectrograms of a radar enables the detection of human activities. The results obtained are from offline processing on databases.

Onboard dimensions and real-time implementation of processing are not addressed. They require the design of classification algorithms taking into account the design of time restrictions on computing time (IO bitrates), and efficient implementation of processing by respecting additional consumption restrictions.

SUMMARY OF THE INVENTION

To meet these objectives, a new system based on the development of a software radar architecture emitting at the frequency (band between 6 MHz and 250 GHz, preferably band 2-4 GHz, more preferably between 2.3 and 2.5 GHz) has been developed (FIG. 1).

The software nature of the radar confers flexibility on the waveform emitted along with the processing of the signals, at the antenna foot. Thus, the processing of radar signatures of micro-Doppler type by image processing and machine learning algorithm solutions can be used to characterize the actimetry of a subject.

The invention relies on the aggregation of several techniques with a view to solving a problem. The inventive step comprises two parts:

A technique for extracting geometrical shape parameters resulting from computer vision techniques, on images of high-resolution micro-Doppler spectrogram type representing speed/distance maps.

A simple classification technique, for example statistical, allowing real-time computation; for example a binary or multiclass classification of SVM type.

The joint use of these two techniques achieves better performance than the state of the art (deep approaches) while guaranteeing a smaller hardware implementation (compatible with a connected object of low computing power) and lower consumption.

This invention discloses a device for characterizing in real time the actimetry of a subject, having:
a radar emitting and receiving radar signals, and having a software interface for configuring the shape of the signal emitted;
processing and computing means coupled to the radar, having a classifier trained using a database.

Said processing and computing means are configured to perform in real time:
a capture of color micro-Doppler images having several color channels (R, V, B), each having micro-Doppler signatures, the intensity values of which are distributed over a gradual scale;
a processing of micro-Doppler images for:
computing a so-called monochromatic image having monochromatic pixels, each having a given monochromatic intensity, on the basis of the color pixels of each color micro-Doppler image;
transforming the monochromatic image into a binary image by segmentation, according to an intensity threshold, of the monochromatic pixels,
by producing binary pixels, the binary value of which for each binary pixel is a function of the value of the chromatic intensity of the monochromatic pixel associated or corresponding to the binary pixel (at the same position on the binary image as the position of the monochromatic pixel on the chromatic image), with respect to the threshold intensity value,
by forming, on the surface of the binary image, segmented areas (or delimited parts of the surface of the binary image) which have binary pixels of the same binary value, and which result from the transformation of each micro-Doppler signature;
computing parameter values on each segmented area, each parameter being solely a parameter that characterizes the geometrical shape of the segmented areas;
classifying each binary image in a class pertaining to the actimetry of the subject, as a function of the values of the parameters computed for all the segmented areas of the binary image, using the trained classifier.

DESCRIPTION OF THE FIGURES

Other features, objectives and advantages will become apparent from the following detailed description with reference to the drawings given by way of illustration and without limitation, among which.

GENERAL DESCRIPTION OF THE INVENTION

This invention relates to a device 1 for characterizing in real time the actimetry of a subject, having:
a radar 2 emitting and receiving radar signals 2, and having a software interface for configuring the shape of the signal emitted;
processing and computing means 3 coupled to the radar 2, having a classifier 3a trained using a database.

Said processing and computing means 3 are configured to perform in real time:
a capture of color micro-Doppler images 6 having several color channels (R, V, B), each having micro-Doppler signatures 6a with color pixels, the intensity values of which are distributed over a gradual scale;
a processing of micro-Doppler images 6 for:
computing a so-called monochromatic image having monochromatic pixels, each having a given monochromatic intensity, on the basis of the color pixels of each color micro-Doppler image;
transforming the monochromatic image into a binary image by segmentation, according to an intensity threshold, of the monochromatic pixels,
by producing binary pixels, the binary value of which for each binary pixel is a function of the value of the chromatic intensity of the monochromatic pixel associated or corresponding to the binary pixel (at the same position on the binary image as the position of the monochromatic pixel on the chromatic image), with respect to the threshold intensity value,
by forming, on the surface of the binary image, segmented areas 5a (or delimited parts of the surface of the binary image) which have binary pixels of the same binary value, and which result from the transformation of each micro-Doppler signature 6a;
computing parameter values on each segmented area 5a, each parameter being solely a parameter that characterizes the geometrical shape of the segmented areas 5a;
classifying each binary image 5 in a class pertaining to the actimetry of the subject, as a function of the values of the parameters computed for all the segmented areas 5a of the binary image 5, using the trained classifier 3a.

The color pixels of the micro-Doppler signatures have an intensity, the value of which is a function of a reflectivity and a speed of the subject, and is distributed over a gradual (in the sense of continuous) scale.

Thus, the conversion of the color Doppler image into the monochromatic image may consist in converting, for each pixel of the color Doppler representation, the triplet of values representing the levels of the primary colors of each color pixel into an integer value which is the sum thereof, and representing a luminosity or a luminous intensity or luminance associated with a representation pixel thus produced.

Each segmented geometrical area thus has first binary pixels of the same value and which stands out against the background of the surface of the binary image.

Specifically, the background of the surface of the binary image also has second binary pixels of the same value but a value different to that of the first binary pixels.

Thus the micro-Doppler signatures are segmented into several segmented geometrical areas.

The computation of similarity for classifying the images can be based on a distance computation in a hyperplane of dimension N where N is the size of the parameters.

This invention aims to avoid performing computations of the prior art on the values represented in the micro-Doppler signatures which are time-consuming, and pertains only to the geometrical shape characteristics of the segmented areas. The transformation by the binarization of the micro-Doppler signatures goes from an item of 3D information to an item of 2D information but makes it possible to perform quick computations and is effective for classifying the images.

This device 1 has storage means 4 coupled to the computing means 3 for storing the classifier 3a, the micro-Doppler images 6, the monochromatic images, the binary images 5 and the classification obtained from the binary images 5.

The processing of the micro-Doppler images 6 can scan each of the binary images in real time with a sliding sub-window;

and for each position of said sliding sub-window, geometrical shape parameters are extracted to classify each sub-image extracted from the binary image under consideration, in a class relating to the actimetry of the subject.

This sub-window is used for the temporal consistency of the classes (or activities extracted) and to conduct tracking; to perform this tracking operation it is necessary to adapt the extraction of geometrical parameters over time.

This adaptation involves modifications of the capturing parameters (such as the measurement time, the luminous intensity, the shape or shapes of the waves) as a function of the segmented areas and of the expected classes, to modify the next segmented areas to arrive.

In an embodiment, the computing of the monochromatic image is performed with the color gray which is a function of the value of the color channels (R, V, B) of the color pixels, for example by following the formula: Gray=0.299*Red+0.587*Green+0.144*Blue, for each pixel of the color micro-Doppler images which has a red intensity value, a green intensity value and a blue intensity value.

Advantageously, the device 1 is configured to continuously characterize the actimetry of the person, the database being continuously supplied and increased with the obtained classification of the binary images 5 performed by the classifier 3a.

Advantageously, the processing and computing means 3 are configured to filter out (delete) the pixels of a same binary value as the pixels of the segmented areas, but located at a distance from the segmented areas 5a.

For example, an erosion and dilation morphological filter is used to remove these isolated pixels, which are located several pixels away from these segmented areas and which are visibly not part of these latters.

The values of the geometrical shape parameter of each segmented area 5a of binary pixels of the same binary value, are not values of frequency, time, speed, or power, measured on the micro-Doppler signatures, as was the case of the prior art.

Advantageously, the classifier 3a of the computing means 3 classifies the images without using neural networks, such as convolutional neural networks (CNN), or multilayer neural networks (DNN), which are too time-consuming.

Advantageously, the device 1 is onboard, and the classifier 3a is in particular chosen from the following list:
  a boosting algorithm;
  an AdaBoost cascade;
  active learning;
  a binary classifier 3a or and/or a cascade of binary classifiers;
  a multi-class classifier (e.g. SVM or Support Vector Machine with cubic kernel).

Boosting includes a set of algorithms such as: AdaBoost, LPBoost, TotalBoost, BrownBoost, xgboost, MadaBoost, and LogitBoost. Boosting is a sequential method and each sample is taken as a function of the performances of the basic rule on the preceding sample. Boosting and its implementation are described in detail in Freund & Schapire 1999 (Machine Learning Large. Margin Classification Using the Perceptron Algorithm). In the context of active learning, a learning algorithm is capable of interactively interrogating the user (or another information source) to obtain the desired outputs at new data points.

The geometrical shape characteristics of each segmented area 5a of binary pixels of the same value are chosen in particular from among the following list: surface, perimeter, first-degree centroid, second-degree centroid, orientation, computing of the zeroth-, first- and second- to nth-order moments, Bounding square, Bounding ellipse etc.

More precisely, for example, one may consider:

Surface=Surface=$\Sigma_x\Sigma_y p_{x,y}$, with $p_{x,y}$ belonging to {shape $i$}

$P_{x,y}$ represents the value of the pixel at the coordinates x,y in the image. The surface counts the number of pixels having the same value '1' in the image. Advantageously, contour detection is obtained by convolutional filtering by Sobel kernel.

Perimeter=Sum of the $p_{x,y}$ belonging to the circumference of the surface. The perimeter is obtained by summing all the pixels of the same value over the contour of the shape. A Sobel operator is used to define the contour of the surface. Thus, the following equation can be used:

Perimeter=$\Sigma x \Sigma y p_x \cdot p_y$ with $x,y \in$ {border of the shape $i$}, zeroth-order moment:

$M0 = \Sigma x \Sigma y p_x^i p_y^j$ with $x,y \in$ {shape $i$} and $i$ and $j=0$ First-degree centroid (first-order moment) corresponding to the center of mass of the shape. It is of coordinates $g_x$ and $g_y$, and computed on the basis of the following equations:

$$gx = \frac{1}{N} \cdot \sum_{k=0}^{N} p_{x_i} \text{ and } gy = \frac{1}{N} \cdot \sum_{k=0}^{N} p_{y_i}$$

with N the total number of pixels in the image, $p_{xi}$ the abscissa of the pixel $p_{yi}$ the ordinate of the pixel.

It can also be obtained according to the following equation:

$$M1=\Sigma x\Sigma y p_x^i\cdot p_y^j \text{ with } x,y\in\{\text{shape } i\} \text{ and } i \text{ and } j=1$$

Second-degree centroid, computed for example on the basis of the following equation:

$$M2=\Sigma x\Sigma y p_x^i\cdot p_y^j \text{ with } x,y\in\{\text{shape } i\} \text{ and } i \text{ and } j=2$$

Orientation: obtained by the determination of the straight line passing through the first-order moment and minimizing the distance of the contour points to the straight line.

EXAMPLES for the surface: counting of the white pixels, zeroth-order moment (means along the x and y axis);
for the perimeter: contour detection (Sobel algorithm)+ counting of the white pixels;
for computing first- and second-order moments:

$$Mm,n=\text{sum}(\text{sum}(x^m y^n f(x,y)dxdy))$$

Bounding square;
Bounding ellipse.
For example Legendre polynomials may be used.

In an embodiment, the segmentation of the pixels is done using a fixed binary threshold. In another embodiment, the segmentation of the pixels is done using a binary threshold which is adaptive or variable as a function of the luminance (example: in the publication Otsu [9]).

The classes may be chosen from among the following list:
walking,
running
standing up,
sitting,
TUG class.

The classes may be chosen from among the following list:
walking with an object carried in both hands,
falling,
sitting on a chair,
tying of shoelaces,
Parkinsons gait,
sitting on the ground,
picking up an object,
searching for an object under a chair,
standing up from a chair and walking.

Advantageously, the computing means 3 are configured to store the successive sequences of classes obtained, and determine an activity map of the subject, particularly using Markov chains, binary or other decision trees, etc.

In an embodiment, the radar 2 is monostatic (one emitter and one receiver).

In another embodiment, the radar 2 is bistatic (one emitter and several receivers.)

The radar 2 emits the radar signals in a frequency band contained between 6 MHz and 250 GHz, preferably between 2 and 4 GHz, more preferably between 2.3 and 2.5 GHz.

The radar software interface can make it possible to emit waves chosen for example from the following categories:
Continuous wave
Frequency-modulated continuous wave: linear and non-linear
Orthogonal frequency division multiplexing
Newman phase codes
M_ary-Phase shift keying
M_ary-Quadrature amplitude modulation
Random carrier phase coding
Optimizing carrier phase coding with genetic algorithms
sparse OFDM
GFDM
Costas frequency coding
Barker codes
Chirplike phase codes
P1, P2 and Px codes
Zadoo-chu code
P3, P4 and Golomb codes
NLFM-based phase codes
Ipatov code
Huffman code
MFSK
Staggered frequency modulated continuous wave
Coherent pulse train
Modulated coherent pulse train
Modulated coherent diverse pulse train
Arbitrary waveforms The threshold adapts with respect to the image created from the signal.

The luminous intensity threshold is related to the waveform emitted and is shaped with respect to the luminous intensities of the color micro-Doppler images, themselves shaped on the basis of the radar signal emitted.

The waveform is configured with respect to the size of the room and the ambiguity, distance and Doppler requirements.

The signal can be configured to be more accurate or less remote, as needed.

The waveforms may be configured so that the codes are orthogonal to avoid interference between radars which might be operating in the same building and thus avoid interference from other surrounding devices.

This invention also relates to a system for controlling the actimetry of a subject, said system comprising:
a building with walls;
a device 1 according to the invention, said device being incorporated into a wall of said building.

The device 1 can be coupled with an alert and control device, able to alert to a need for an intervention on the subject whose actimetry is being monitored, if the sequence of classes of the binary images 5, determined in real time, indicates a risk-related behavior as activity map.

As mentioned above, in said system the device 1 includes:
one or more monostatic radars; and/or
one or more bistatic radars.

Figure 2:
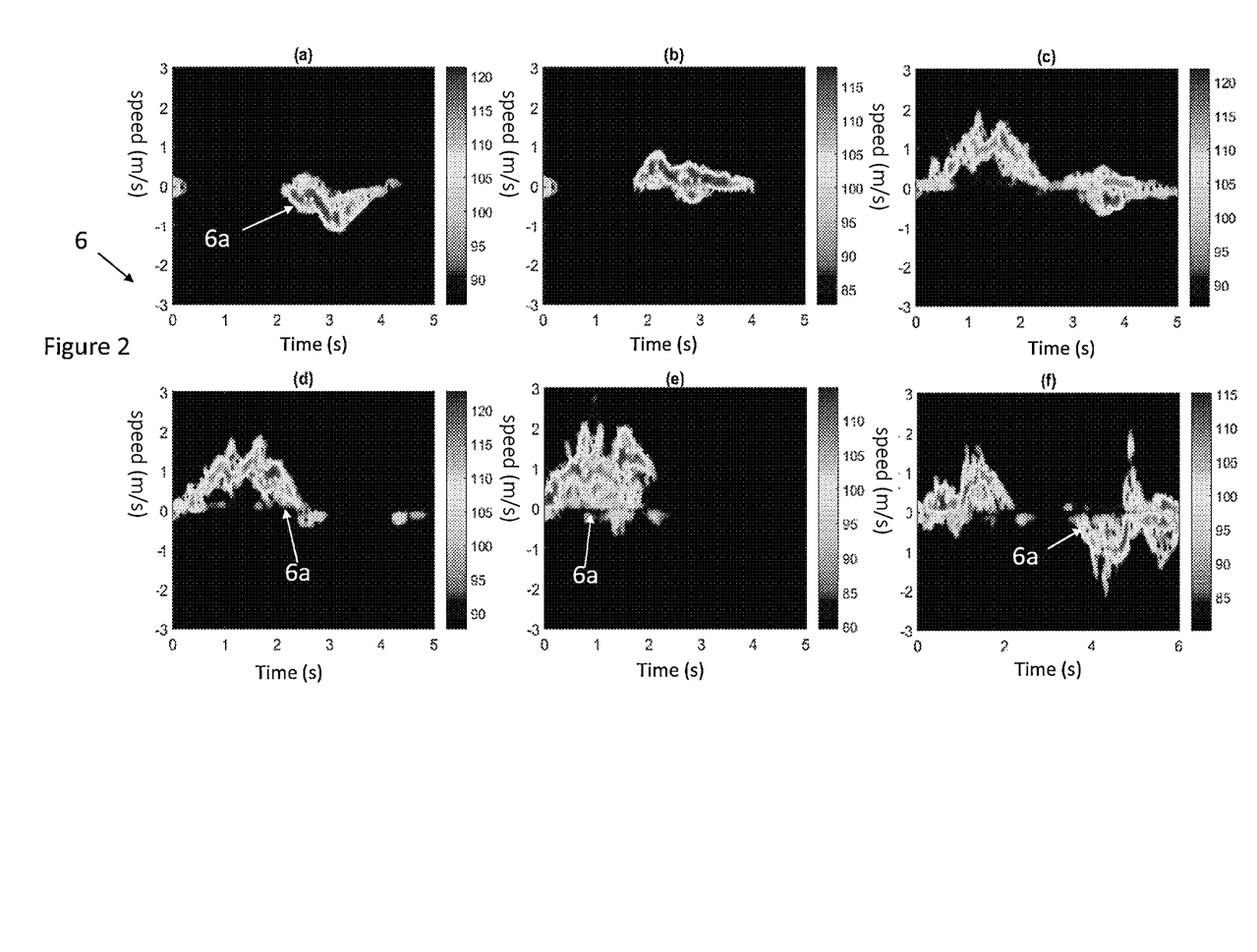
FIG. 2 shows micro-Doppler signatures which will be processed by the device and method of the invention; the micro-Doppler signatures are as follows: (a) Sitting on a chair; (b) Standing up from a chair; (c) Bending and picking up a pen on the ground; (d) Bending and tying of shoelaces; (e) Falling forward; (f) Squatting to look over and under an item of furniture.

First processing has been developed for the recognition of the actimetry of a subject. A database has been compiled on the basis of a software radar 2 prototype, composed of 10 classes (walking, walking with an object carried in both hands, fall, sitting on a chair, tying of shoelaces, Parkinsons gait, sitting on the ground, picking up an object under a chair, standing up from a chair and walking), of 5 subjects. 10 characteristics are then extracted from the images corresponding to geometrical shape parameters (surface, perimeter, first-degree centroid, second-degree centroid, orientation etc.), 70% of the characteristics extracted have been used to train statistical models (SVM—Support Vector Machine with cubic kernel) (FIG. 2).

Figure 3:
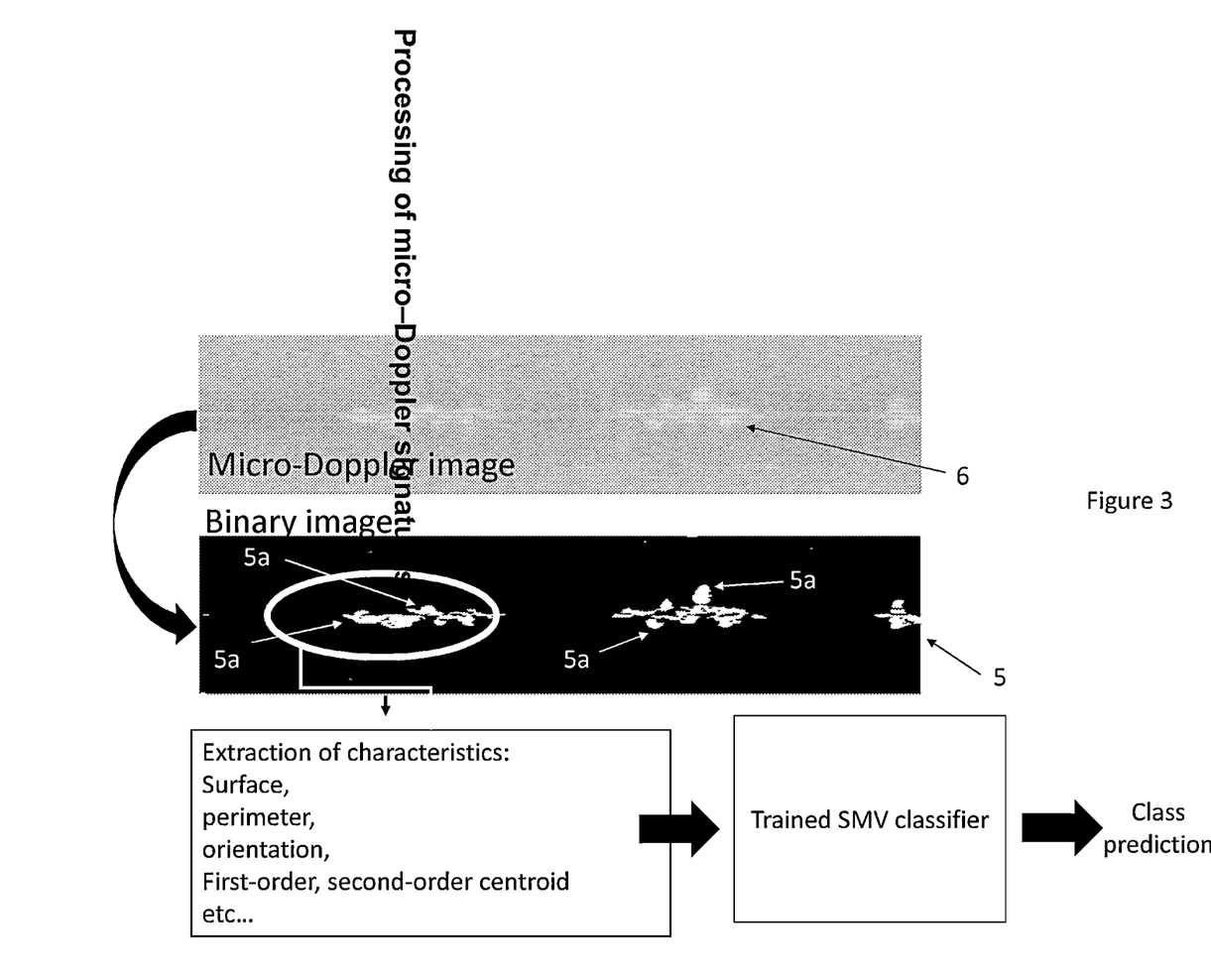
FIG. 3 shows an algorithmic chain for and which is the subject of this invention.
Figure 4:
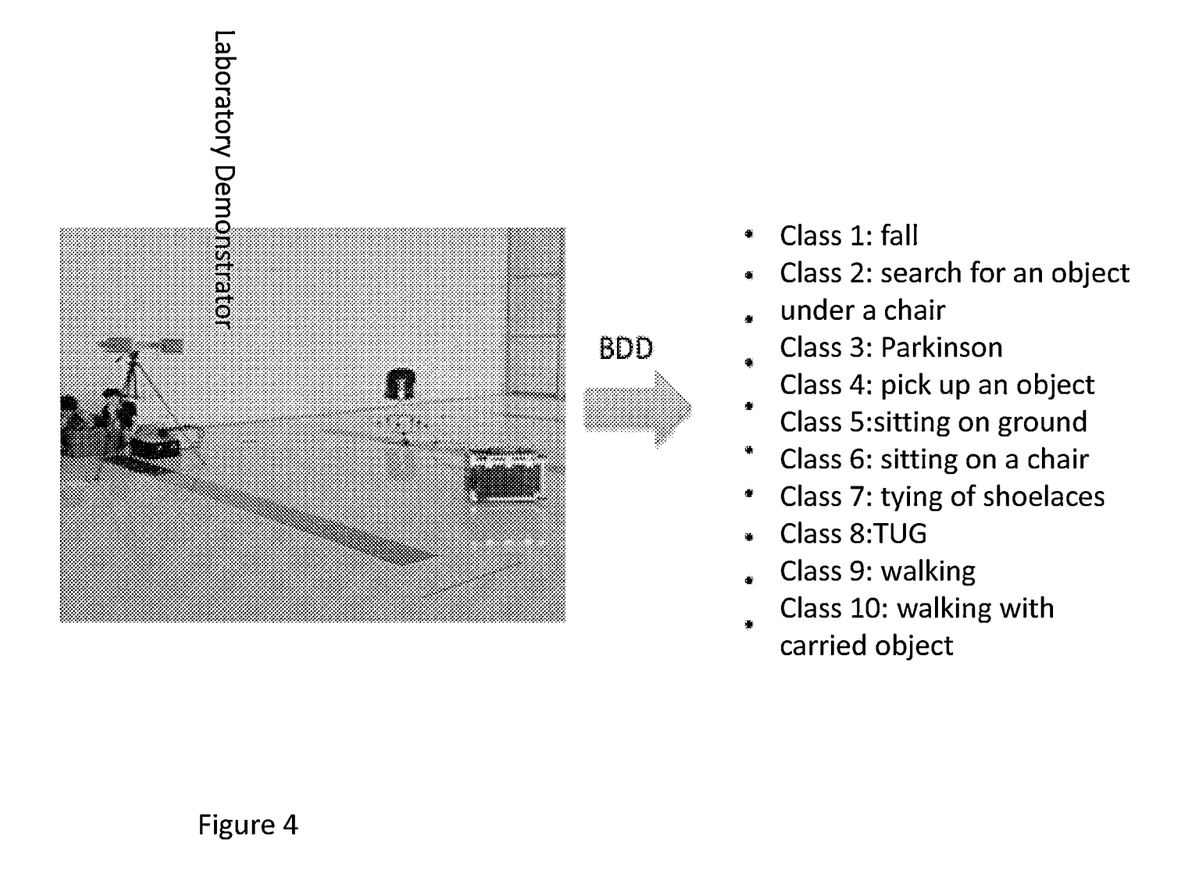
FIG. 4 shows a laboratory proof of concept and the classes under consideration.
Figure 5:
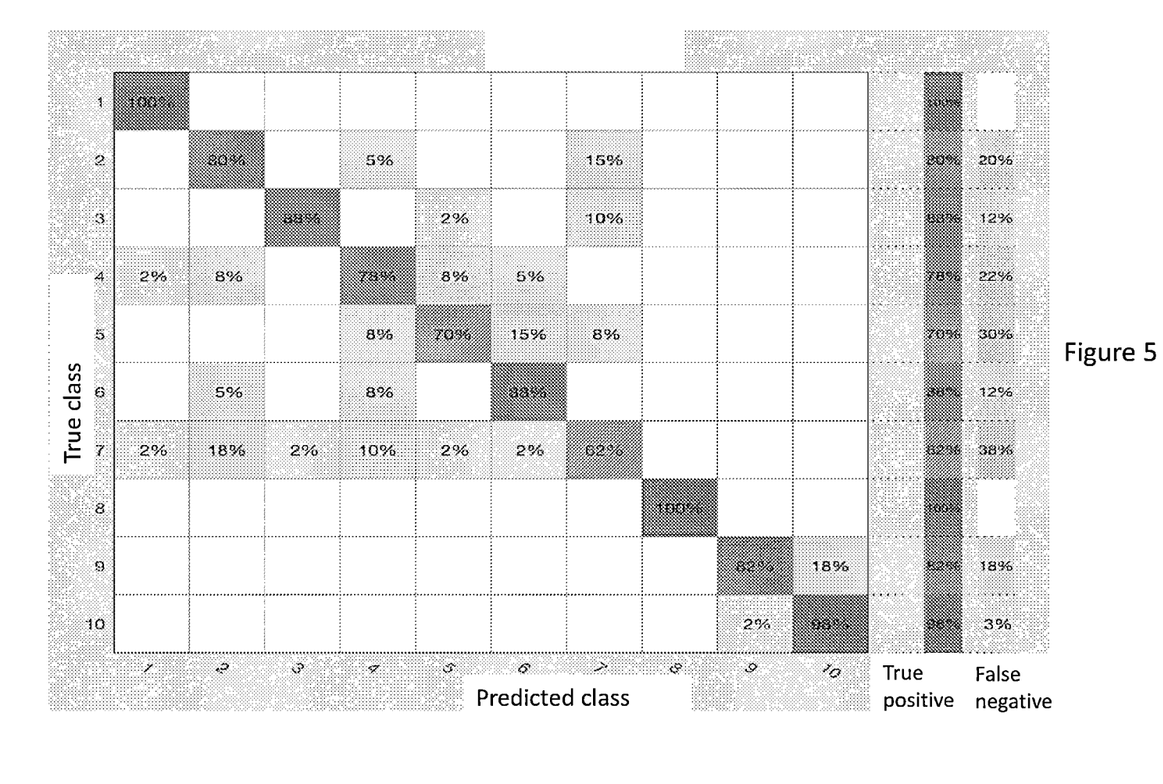
FIG. 5 shows a confusion matrix.

Starting from the database, the accuracy over all the 10 classes is of 84.5% (FIG. 3). These results are comparable to those obtained by convolutional neural networks—CNN—but with a lower algorithmic complexity, making them more optimized for real-time implementation.

Main Applications of the Invention

1. Detection of falls in the home, in a residential care home for the elderly and in the hospital environment.
2. Assistance with evaluation of gait impairment for health professionals (physical therapists for example).

The quantification of tests used in clinical practice to detect any pathology or fragility. The three main tests are the TUG (Time Up and Go), the one-leg stance test and the Tinetti test. These tests are used to supply an evaluation of the quality of the gait and the balance of the subject to thus evaluate the subject's state. On the basis of the images from the spectrograms, it is possible to compute the TUG class, that of the one-leg stance test or that of the Tinetti test.

Then, once the TUG class has been identified for example, it is possible to extract specific metrics and objectify the TUG measurements, in particular. The first results are used to identify a TUG test with 100% accuracy. To do this, additional metrics must be defined to extract metrological qualities from the TUG.

The repeated observation of the activity of a subject over time will make it possible to identify the signs of degradation in gait. After identifying the class of the activity (walking, slow walking etc.) gait metrics can be extracted from the spectrograms to characterize its biomechanical behavior such as step length, walking speeds (min, max, average) spatio-temporal asymmetry, walking pace and the variation in the center of gravity. The monitoring of these parameters is used to detect variations in behavior and identify degradations that can lead to falls.

3. Detection of Suicides in a Penitentiary Environment

The real-time monitoring of the activity of high-risk inmates on the basis of the solution presented here will make it possible to anticipate extreme suicide situations (risk seven times higher than in the rest of the population) by identifying the characteristic signatures of the activity.

PUBLICATIONS CITED

[1] M. G. Amin, Y. D. Zhang, F. Ahmad, and K. C. D. Ho, "Radar 2 Signal Processing for Elderly Fall Detection: The future for in-home monitoring," *IEEE Signal Processing Magazine*, vol. 33, no. 2, pp. 71-80, 2016.
[2] (2012). *Report to Congress: Aging services Technology Study*.
[3] C. Debes, A. Merentitis, S. Sukhanov, M. Niessen, N. Frangiadakis, and A. Bauer, "Monitoring Activities of Daily Living in Smart Homes: Understanding human behavior," *IEEE Signal Processing Magazine, vol.* 33, no. 2, pp. 81-94, 2016.
[4] H. Li, A. Shrestha, F. Fioranelli, J. L. Kernec, and H. Heidari, "Multisensory Data Fusion for Human Activities Classification and Fall Detection," presented at the IEEE Sensors 2017, Glasgow, UK, 30 Oct.-1 Nov. 2017.
[5] E. Cippitelli, F. Fioranelli, E. Gambi, and S. Spinsante, "Radar 2 and RGB-Depth Sensors for Fall Detection: A Review," *IEEE Sensors* Journal, vol. 17, no. 12, pp. 3585-3604, 2017.
[6] E. Cippitelli, F. Fioranelli, E. Gambi, and S. Spinsante, "Radar 2 and RGB-Depth Sensors for Fall Detection: A Review," *IEEE Sensors Journal*, vol. 17, no. 12, pp. 3585-3604, 2017.
[7] M. G. Amin, Y. D. Zhang, F. Ahmad, and K. C. D. Ho, "Radar 2 Signal Processing for Elderly Fall Detection: The future for in-home monitoring," *IEEE Signal Processing Magazine*, vol. 33, no. 2, pp. 71-80, 2016.
[8] B. Jokanović and M. Amin, "Fall Detection Using Deep Learning in Range-Doppler Radar 2s," *IEEE Transactions on Aerospace and Electronic Systems*, vol. PP, no. 99, pp. 1-1, 2017.
[9] Nobuyuki Otsu, «A threshold selection method from gray-level histograms», IEEE Trans. Sys., Man., Cyber., vol. 9, 1979, p. 62-66

The invention claimed is:

1. A device for characterizing in real time actimetry of a subject, having:
   a radar emitting and receiving radar signals, and having a software interface for configuring a shape of the signal emitted;
   means for processing and computing coupled to the radar, having a classifier trained using a database,
   said means for processing and computing being configured to perform in real time:
   a capture of color micro-Doppler images having several color channels, each having micro-Doppler signatures with color pixels;
   a processing of micro-Doppler images for:
      computing a monochromatic image having monochromatic pixels, each having a given monochromatic intensity, on the basis of the color pixels of each color micro-Doppler image;
      transforming the monochromatic image into a binary image by segmentation, according to a binary luminous intensity threshold, of the monochromatic pixels,
   by producing binary pixels, a binary value of which for each binary pixel is a function of a value of chromatic intensity of the monochromatic pixel associated with the binary pixel, with respect to the binary luminous intensity threshold,
   by forming, on a surface of the binary image, segmented areas which have binary pixels of the same binary value, and which result from the transformation of each micro-Doppler signature;
      computing geometrical shape parameter values on each segmented area, each geometrical shape parameter being solely a parameter that characterizes a geometrical shape of segmented areas,
      classifying each binary image in a class pertaining to the actimetry of the subject, as a function of the values of the parameters computed for all the segmented areas of the binary image, using the classifier trained with these geometrical shape parameters computed over segmented areas of binary images of test subjects having a known actimetry,
   means for storing coupled to the means for processing and computing for storing the classifier, the micro-Doppler images, the monochromatic images, the binary images and the classification obtained from the binary images.

2. The device according to claim 1, wherein the geometrical shape parameters of each segmented area of binary pixels are chosen from among the following list:
   surface,
   perimeter,
   first-degree Centroid,
   second-degree Centroid,
   orientation,
   Computing of the zeroth-, first- and second- to nth-order moments,
   Bounding square, and/or
   Bounding ellipse.

3. The device according to claim 1, said binary luminous intensity threshold being variable as a function of the luminance.

4. The device according to claim 1, wherein the segmentation of the pixels is done using said binary luminous intensity threshold according to the Otsu method.

5. The device according to claim 1, said binary luminous intensity threshold being fixed.

6. The device according to claim 1, wherein the classifier is a binary classifier and/or a cascade of binary classifiers.

7. The device according to claim 1, wherein the classifier is a multi-class classifier.

8. The device according to claim 1, wherein the device is configured to continuously characterize the actimetry of the subject, the database being continuously supplied with the classification obtained from the binary images of the subject with the geometrical shape parameters applied to each segmented area and performed by the classifier on the basis of the micro-Doppler images.

9. The device according to claim 1, wherein the means for processing and computing are configured to filter out the pixels of a same binary value as the pixels of the segmented areas, but located at a distance from the segmented areas.

10. The device according to claim 1, wherein the device is onboard.

11. The device according to claim 1, wherein processing of the micro-Doppler images scans each of the binary images in real time with a sliding sub-window;
and for each position of said sliding sub-window, geometrical shape parameters are extracted to classify each sub-image extracted from the binary image under consideration, in a class relating to the actimetry of the subject.

12. The device as claimed in claim 11, wherein the processing of the micro-Doppler images makes it possible, with the sliding sub-window, to carry out tracking to modify capturing parameters as a function of the segmented areas and of expected classes, to modify the next segmented areas to arrive.

13. The device according to claim 1, wherein the computing of the monochromatic image is performed in shades of gray, said shades of gray being a function of a value of the color channels of the color pixels.

14. The device according to claim 1, wherein the computing of the monochromatic image is performed with the color gray which is a function of a value of the color channels of the color pixels, following the formula: Gray=0.299*Red+0.587*Green+0.144*Blue, for each pixel of the color micro-Doppler images which has a red intensity value, a green intensity value and a blue intensity value.

15. The device according to claim 1, wherein the class is chosen from among the following list:
walking,
running
standing up,
sitting,
TUG class,
walking with an object carried in both hands
falling,
sitting on a chair,
tying of shoelaces,
Parkinsons gait,
sitting on the ground,
picking up an object,
searching for an object under a chair,
standing up from a chair and walking.

16. The device according to claim 1, wherein the means for storing are configured to store successive sequences of classes obtained, and to determine an activity map of the subject.

17. The device according to claim 1, wherein the radar emits the radar signals in a frequency band between 6 MHz and 250 GHz.

18. A system for controlling actimetry of a subject, said system comprising:
a building with walls;
a device for characterizing in real time the actimetry of said subject, said device being incorporated into a wall of said building and having:
a radar emitting and receiving radar signals, and having a software interface for configuring a shape of the signal emitted;
means for processing and computing coupled to the radar, having a classifier trained using a database,
said means for processing and computing being configured to perform in real time:
a capture of color micro-Doppler images having several color channels, each having micro-Doppler signatures with color pixels;
a processing of micro-Doppler images for:
computing "monochromatic image" having monochromatic pixels, each having a given monochromatic intensity, on the basis of the color pixels of each color micro-Doppler image;
transforming the monochromatic image into a binary image by segmentation, according to a binary luminous intensity threshold, of the monochromatic pixels,
by producing binary pixels, a binary value of which for each binary pixel is a function of a value of a chromatic intensity of the monochromatic pixel associated with the binary pixel, with respect to the binary luminous intensity threshold,
by forming, on the surface of the binary image, segmented areas which have binary pixels of the same binary value, and which result from the transformation of each micro-Doppler signature;
computing geometrical shape parameter values on each segmented area, each geometrical shape parameter being solely a parameter that characterizes the geometrical shape of segmented areas,
classifying each binary image in a class pertaining to the actimetry of the subject, as a function of the values of the parameters computed for all the segmented areas of the binary image, using the classifier trained with these geometrical shape parameters computed over segmented areas of binary images of test subjects having a known actimetry,
means for storing coupled to the means for processing and computing for storing the classifier, the micro-Doppler images, the monochromatic images, the binary images and the classification obtained from the binary images.

19. The system according to claim 18, wherein the device is coupled with an alert and control device, adapted to alert to a need for an intervention on the subject whose actimetry is being monitored, if a sequence of classes of the binary images, determined in real time, indicates a risk-related behavior as activity map.

20. The system according to claim 18, wherein the device includes:
one or more monostatic radars; and/or
one or more bistatic radars.

* * * * *